United States Patent [19]
Ebert et al.

[11] Patent Number: 5,152,997
[45] Date of Patent: Oct. 6, 1992

[54] METHOD AND DEVICE FOR TRANSDERMALLY ADMINISTERING TESTOSTERONE ACROSS NONSCROTAL SKIN AT THERAPEUTICALLY EFFECTIVE LEVELS

[75] Inventors: Charles D. Ebert, Salt Lake City; Dinesh Patel, Murray; Werner Heiber, Salt Lake City, all of Utah

[73] Assignee: Theratech, Inc., Salt Lake City, Utah

[21] Appl. No.: 652,127

[22] Filed: Feb. 7, 1991

Related U.S. Application Data

[63] Continuation-in-part of Ser. No. 626,685, Dec. 11, 1990.

[51] Int. Cl.⁵ ............................................. A61F 13/00
[52] U.S. Cl. .................................... 424/449; 424/448; 424/441
[58] Field of Search ................ 424/449, 448, 447, 486

[56] References Cited

U.S. PATENT DOCUMENTS

| | | | |
|---|---|---|---|
| 4,704,282 | 11/1987 | Campbell et al. | 424/449 |
| 4,863,970 | 9/1989 | Patel et al. | 514/754 |
| 4,867,982 | 9/1989 | Campbell et al. | 424/449 |
| 4,906,963 | 3/1990 | Cleary et al. | 424/78 |
| 4,911,916 | 3/1990 | Cleary | 424/447 |

OTHER PUBLICATIONS

Korenman et al., *Am. J. Med.* (1987) 83:471–478.
Ahmed et al., *J. Clin. Endocrinol. Metab.* (1988) 66:546–557.
Findlay, *J. Clin. Endocrinol. Metab.* (1989) 68:369–373.

Primary Examiner—Thurman K. Page
Assistant Examiner—Leon R. Horne
Attorney, Agent, or Firm—Morrison & Foerster

[57] ABSTRACT

Testosterone is administered transdermally through nonscrotal skin in a manner that mimics in amount and profile the natural production of testosterone in young adult healthy males. The testosterone is administered to the skin from a matrix which contains testosterone at subsaturation concentration and a permeation enhancer.

15 Claims, 9 Drawing Sheets

5,152,997

METHOD AND DEVICE FOR TRANSDERMALLY ADMINISTERING TESTOSTERONE ACROSS NONSCROTAL SKIN AT THERAPEUTICALLY EFFECTIVE LEVELS

CROSS-REFERENCE TO RELATED APPLICATION

This application is a continuation-in-part of U.S. application Ser. No. 626,685, filed Dec. 11, 1990, the disclosure of which is incorporated herein by reference.

TECHNICAL FIELD

This invention is in the field of transdermal drug delivery. More particularly, it is directed to methods and devices for providing transdermal delivery of testosterone across unbroken nonscrotal skin at flux levels exceeding 2 $\mu g/cm^2/hr$.

BACKGROUND

Testosterone therapy is currently indicated for treatment of male hypogonadism, anemia, breast cancer, and hereditary angioedema. It is also being considered for treating a variety of other conditions such as male osteoporosis that appear to be mediated by androgen deficiency.

Traditional modalities for administering testosterone have included: intramuscular injection of long-acting testosterone esters such as the enanthate because testosterone itself is rapidly degraded by the liver if administered orally; oral administration of testosterone undecanoate, which provides systemically available testosterone; and subcutaneous implantation of fused testosterone pellets. None of these traditional modalities provides totally physiological levels or circadian patterns of testosterone and its active metabolites, dihydrotestosterone (DHT) and estradiol ($E_2$).

It is known that steroids, including testosterone, are absorbed through skin. However, the permeability to testosterone of skin areas that are normally used for transdermal delivery (e.g., the neck, back, chest, arms) is too low to permit delivery of the amounts of testosterone needed for therapy (typically 5–10 mg/day) through a limited area of skin. In this regard, Korennan, S. G., et al., (Am J Med (1987) 83:471–478) in an article on testosterone delivery for treating hypogonadism concluded "a more permeable skin area with a much higher absorption rate was required to provide programmed transdermal delivery to a limited area." This led Korennan et al. to select scrotal skin—which is highly permeable to testosterone—as a site for testosterone delivery. The article further describes a transscrotal delivery system developed by ALZA Corporation. U.S. Pat. No. 4,704,282 describes that system in detail. It consists of a polymer matrix that contains testosterone at subsaturation levels and a fabric reinforcement incorporated into the matrix that also is a limited solvent for testosterone. The patent indicates that a subsaturated matrix is used because a declining testosterone release rate is desired. The reinforcing fabric, in addition to providing a structural support function, is said to act as a secondary reservoir for testosterone which has the effect of flattening the release rate profile (see FIG. 2 of the patent). While the patent states that permeation enhancers may be present in the matrix, no examples of the use of such enhancers are described. The patent gives no data on the skin flux of testosterone provided by its systems. Example 2 of the patent states that its system may be applied to nonscrotal skin, particularly the thigh, to produce "similar results" as when applied to scrotal skin. This statement is, however, contradicted by the later Korennan et al. article (which also originates from ALZA Corporation) which reports that systems applied to the thigh did not give increased blood levels of testosterone.

Ahmed, S. R., et al. (J Clin Endocrinol Metab (1988) 66:546–557) and Findlay, J. C. (J Clin Endocrinol Metab (1989) 68:369–373) report that the 60 $cm^2$ ALZA transscrotal system delivers about 3.7 mg/day and produces low-normal testosterone levels in hypogonadal men. Such dosages are believed to be somewhat less than the amount needed to mimic endogenous production (5–10 mg/day). Furthermore, since scrotal skin has a relatively high level of 5$\alpha$-reductase, continuous transscrotal delivery of testosterone produces levels of DHT and DHT/testosterone ratios 4- to 5-fold greater than normal. Such abnormal levels and ratios may give rise to undesirable side effects.

In sum, the art teaches away from transdermally administering testosterone through nonscrotal skin because of the low permeability of such skin to testosterone. Transscrotal delivery of testosterone is taught, but such delivery is associated with high DHT and DHT/testosterone ratio levels and does not provide a level of testosterone delivery that mimics endogenous production. Further, scrotal skin is sensitive and limited in area, which may result in discomfort and poor patient acceptance of this modality of delivery.

DISCLOSURE OF THE INVENTION

Contrary to the teachings of the prior art, the present applicants have discovered means by which testosterone may be administered transdermally through unbroken nonscrotal skin at therapeutically effective levels. Accordingly, the invention provides methods and devices for achieving such administration.

One aspect of the invention is a method of providing testosterone therapy to a human by administering testosterone transdermally across nonscrotal skin of said human wherein the flux of testosterone through said nonscrotal skin is greater than 2 $\mu g/cm^2/hr$.

Another aspect of the invention is a method of treating hypogonadism in a male human comprising administering testosterone transdermally through nonscrotal skin of said male human in a manner that provides blood levels of testosterone and its active metabolites in said male that correspond substantially to endogenous blood levels produced by healthy young adult male humans.

Another aspect of the invention is a device for administering testosterone transdermally across an area of unbroken nonscrotal skin at a flux greater than 2 $\mu g/cm^2/hr$ comprising:

(a) a reservoir comprising testosterone dissolved in a carrier, and a skin permeation enhancer, the amount and solubility of testosterone in the carrier defining a condition of subsaturation that causes enhanced permeation of testosterone through nonscrotal skin and wherein the combined permeation enhancement resulting from said condition of subsaturation and said permeation enhancer provide said flux; and (b) means for maintaining the reservoir in diffusional communication with said area of unbroken nonscrotal skin.

MODES FOR CARRYING OUT THE INVENTION

The term "flux" intends the rate of transfer of testosterone across skin as measured by the method of Merritt and Cooper (J Controlled Release (1984) 1:161). The units of flux are preferably $\mu g/cm^2/hr$.

The term "nonscrotal skin" means human skin excepting the skin of the male human genitalia. It will normally denote the skin of relatively hair-free portions of the body such as the limbs, back, chest, buttocks, hips, and neck.

As used here, the term "testosterone therapy" intends treatment of any indication for which testosterone is indicated, including, without limitation, primary, secondary and other male hypogonadal states in adults and adolescents, anemia, hereditary angioedema, male contraception, male infertility disorders, post-surgical recovery, male impotence, hormone replacement in elderly males, and hypogonadal states associated with AIDS. Primary (testicular) hypogonadism disorders include Klinefelder's Syndrome, viral orchitis, and low testosterone production caused by trauma, radiation or chemotherapy, or alcohol abuse. Secondary (hypothalamic/pituitary) disorders include those associated with hypothalamic hypogonadism, suprasellar tumors, and pituitary tumors. Other male hypogonadism disorders include those associated with aging, systemic illnesses, stress, and diabetes mellitus.

Figure 7:
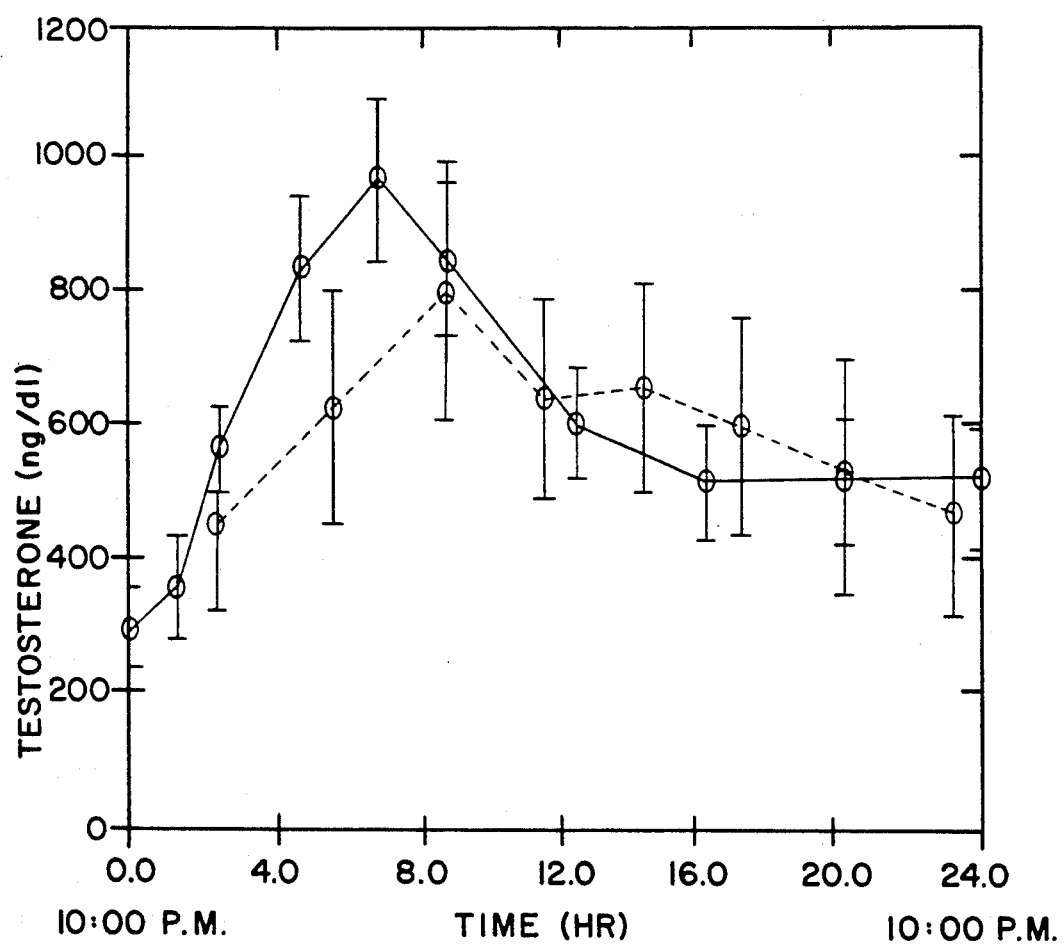
FIGS. 7, 8 and 9 are graphs of data described in Example 3.

The phrase "corresponds substantially to endogenous blood levels produced by healthy young adult male humans" intends a blood level profile that closely approximates the circadian rhythm of testosterone production shown in FIG. 7 of the drawings.

The devices of the invention release drug continuously by diffusion. In this mode, the driving force is the difference in testosterone activity between the device reservoir and the skin and underlying tissue. The testosterone, which is entirely dissolved in the carrier or vehicle in the case of the present invention, permeates through the carrier to the skin. The solution is, of course, in diffusional communication with the skin—which means that it either contacts the skin directly or contacts material interposed between the solution and the skin that provides a permeation pathway for the testosterone and permeation enhancer to migrate from the reservoir to the skin. The interposed material may be homogeneous, heterogeneous, or be composed of a multiplicity of distinct layers. In any event, the interposed material is permeable to the testosterone and permeation enhancer and preferably is not a rate-controlling barrier to diffusion (i.e., it is at least as permeable to the testosterone and enhancer as the carrier).

As indicated above, the carrier or vehicle is permeable to testosterone and the permeation enhancer. In this regard the diffusion coefficient of testosterone in the carrier will usually be between $1 \times 10^{-6}$ and $1 \times 10^{-12}$ cm$^2$/sec, more usually between $1 \times 10^{-7}$ and $1 \times 10^{-10}$ cm$^2$/sec The solubility of testosterone in the carrier should be such that sufficient testosterone is contained in the device to provide the required cumulative dose of testosterone, which will normally be in the range of 5 to 10 mg/day. At the same time, the solubility should not be so low as to require the device to be impractically large in area or thickness. In most instances, the solubility of testosterone in the carrier will be in the range of 1 to 500 mg/ml, more usually 1 to 200 mg/ml (measured at room temperature). The amount of testosterone in the carrier will normally range between 5 and 50 mg per unit dosage form, more usually between 10 and 20 mg. The thickness of the reservoir will usually be about 0.01 to 5 mm, more usually 0.03 to 2 mm. The area of the device in drug delivery contact with the skin will usually be between about 1 and 150 cm$^2$, more usually between 5 and 40 cm$^2$. The required dosing may be supplied by a single device or by a plurality of devices applied to the skin.

Preferably, the carrier is a fluid (e.g., liquid, gel, emulsion, suspension). It may be aqueous or nonaqueous. Examples of fluid carriers that may be used are alcohols such as ethanol, alcohol-water mixtures, and low molecular weight polymers such as polyethylene glycol. Ethanol is preferred and also provides permeation enhancement. In the case of ethanol, the carrier normally constitutes 20% to 70% by volume of the reservoir, more usually 40% to 60%, and preferably approximately 50%. Alternatively, the carrier may be a solid or semisolid matrix such as a pressure-sensitive adhesive.

The skin testosterone flux provided by the invention is at least about 2 $\mu g/cm^2/hr$, more usually about 5 to 30 $\mu g/cm^2/hr$, and preferably about 10 to 20 $\mu g/cm^2/hr$. In contrast, the testosterone skin flux provided by conventional transdermal administration is typically less than 0.5 $\mu g/cm^2/hr$. The high skin fluxes realized through the invention are a result of enhancement due to the subsaturation concentration of testosterone in the carrier and the enhancement due to the permeation enhancer.

For treating male hypogonadism it is desired to provide daily administration in a 24-hr release rate profile that mimics the endogenous diurnal testosterone production pattern. This in turn leads to a circadian rhythm in testosterone levels. FIG. 7 of the drawings (open circles) shows a representative circadian rhythm of testosterone production over a one-day period. As shown, testosterone levels peak in the early morning hours and then decline to trough values in the evening.

The initial concentration of testosterone in the carrier will usually be between 10% and 80% of saturation concentration, usually 15% and 30% of saturation. Depending upon the nature of the carrier and the permeation enhancers, the concentration of testosterone relative to saturation may decrease or increase over the administration period. If the solubility of testosterone in the carrier (whether modified or not by the permeation enhancer) remains constant over the period, the concentration relative to saturation will decrease. On the other hand, if the solubility decreases (for instance, through delivery of a permeation enhancer that also increases solubility), then the concentration relative to saturation will increase.

A permeation enhancer is administered concurrently with the drug in order to further increase the flux of testosterone across the skin. The enhancer may also be contained within the reservoir or be administered from a separate reservoir underlying or overlying the testosterone reservoir. For design simplicity, the enhancer will preferably be contained in the testosterone reservoir. Aside from the requirements that the enhancer be compatible with testosterone and carrier, there are no limitations on the enhancers that may be used in the invention. Examples of enhancers known in the art are those described in U.S. Pat. Nos. 3,989,816; 4,316,893; 4,863,970; 4,764,379; 4,537,776; and EPA (Pub. No.) 272,987, the disclosures of which, as they relate to enhancers, are incorporated herein by reference. A preferred enhancer is a mixture of ethanol (also carrier), glycerol monooleate (GMO) and methyl laurate (ML). The amounts of each of GMO and ML in the reservoir will normally be 0.5% to 5% by volume, preferably approximately 2.5%. The amount of ethanol will be that previously described. The reservoir may also contain amounts of other materials such as gelling agents and antiirritants. Glycerin is a preferred antiirritant and may be present at 5% to 50%, preferably 20% to 30% by volume. The use of glycerin as an anti-irritant is described in U.S. Pat. No. 4,855,294.

The device of the invention may be embodied in various types of structures known in the transdermal drug delivery art. For instance, the testosterone reservoir, which is the most important component of the device, may comprise a gelled liquid solution or suspension containing testosterone at subsaturation levels and an enhancer within a carrier or be in the form of a fibrous body impregnated with the subsaturated solution of drug in the carrier. In addition to the reservoir, the device includes means for maintaining the reservoir in diffusional communication with the skin. Such means include a carrier which is also an adhesive, a separate basal adhesive layer underlying the reservoir, a peripheral ring of adhesive that is interconnected to the reservoir, an adhesive overlay for the reservoir, and straps. Preferably the means is either an adhesive carrier or a separate underlying adhesive layer.

In addition to the reservoir and affixation means, the device may further include a backing that overlies the reservoir and protects the reservoir and/or prevents back-diffusion of testosterone and enhancer from the reservoir, one or more structural layers to provide the device with appropriate mechanical properties, and/or a release liner layer that underlies the reservoir and which is removed prior to use and means for affixing the device to the skin. Preferred embodiments of the device have the general structure described in U.S. Pat. No. 4,849,224. Alternate designs would include matrix-type patches.

These devices may be manufactured by conventional techniques used in the transdermal drug delivery device art. For instance testosterone, permeation enhancer and carrier may be mixed in the desired proportions to form a homogeneous mixture and cast or otherwise applied to a backing layer, followed by lamination to a release liner layer. If a separate basal adhesive layer is desired, it may be cast onto the release liner layer prior to such lamination. As indicated above, the solubility of testosterone in the carrier and the size (thickness of reservoir and area in diffusional communication with the skin) are chosen to maintain subsaturation in the reservoir over the desired dispensing lifetime of the device and provide the necessary cumulative dose of testosterone.

The following examples further illustrate the invention and its unique characteristics. These examples are not intended to limit the invention in any manner. In the following examples in vitro steady state transdermal flux across human cadaver skin was determined using the method of Merritt and Cooper, supra. Unless otherwise indicated percentages and proportions are by volume.

EXAMPLE 1

Formulations of testosterone at saturation and below saturation were prepared by mixing testosterone with carrier and enhancer and applied to nonscrotal human cadaver skin. The carrier and enhancer(s) used were EtOH/H$_2$O/Gly/GMO/ML in a ratio of 60/30/5/2.5/2.5. (Gly=glycerine; GMO=glycerol monooleate; ML=methyl laurate; EtOH=ethanol.) The results of these tests are shown in Table 1 below. The formulations containing 50 mg/ml testosterone were saturated, whereas the formulations containing 40 mg/ml and below were subsaturated. The results are expressed in terms of cumulative permeations at 24 hr (i.e., $\mu$g/cm$^2$) rather than as flux.

TABLE 1

| | Conc. (mg/ml) Cumulative Permeation at 24 hr ($\mu$g/cm$^2$) | | | | | | |
|---|---|---|---|---|---|---|---|
| Skin | 50 | 40 | 30 | 20 | 15 | 10 | 5 |
| 1 | 156.04 | 189.44 | 244.37 | 298.68 | — | 340.93 | — |
| 2 | 188.24 | — | — | 407.57 | — | 564.62 | 335.57 |
| 3 | 121.68 | — | — | 317.66 | 550.48 | 386.73 | — |
| 4 | 128.25 | — | — | 429.22 | 386.89 | 281.79 | — |
| 5 | 130.98 | — | — | 232.71 | 212.18 | 262.63 | — |
| Mean | 145.04 | 189.44 | 244.37 | 337.17 | 383.18 | 367.34 | 335.57 |
| SD | 24.55 | — | — | 72.39 | 138.14 | 107.96 | — |

EXAMPLE 2

Five-layer laminated composites of the general structure described in U.S. Pat. No. 4,849,224 were prepared. The layers of the composite (basal to top) were as follows:
1. 5 mil thick silicon-coated polyethylene terephthalate (Tekkote) release liner
2. 1.5 mil thick pressure-sensitive adhesive (AR MA31 acrylic, Adhesives Research)
3. 4 mil thick peel seal disc of ethylene/vinyl acetate copolymer film (Bertek 2216)
4. 2 mil thick microporous polyethylene film (Cotran, 3M) and a 4-5 mil thick cavity (5 cm$^2$ surface area) filled with an ointment composed of 6.06 mg micronized testosterone, 296.88 mg ethanol, 200.10 mg water, 38.31 mg glycerin, 5.64 mg GMO, 5.27 mg ML, 0.6I mg Vitamin E, and 12.13 mg Klucel.
5. 2 mil thick polyester/ethylene-vinyl acetate laminate (3M Scotchpak 1012) film backing The release liner and peel seal disc are removed for application to skin. The basal surface area of the reservoir was 5 cm$^2$.

Figure 1:
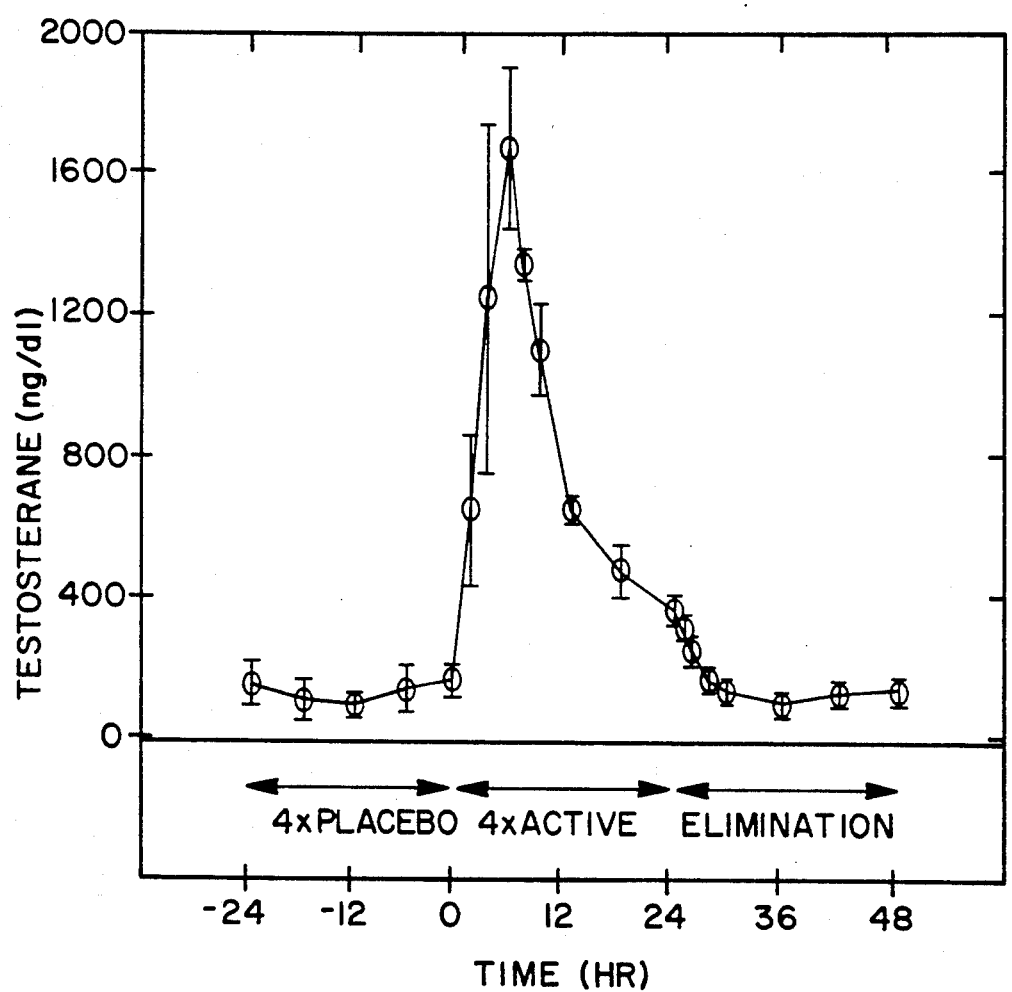
FIGS. 1 and 2 are graphs of the results of the tests described in Example 2.

Placebo composites (four each) and the above composites (four each) were placed on the lower back skin of three hypogonadal men according to the regimen shown in FIG. 1. Periodic blood samples were taken and analyzed for testosterone and DHT levels using established radioimmunoassays.

Figure 2:
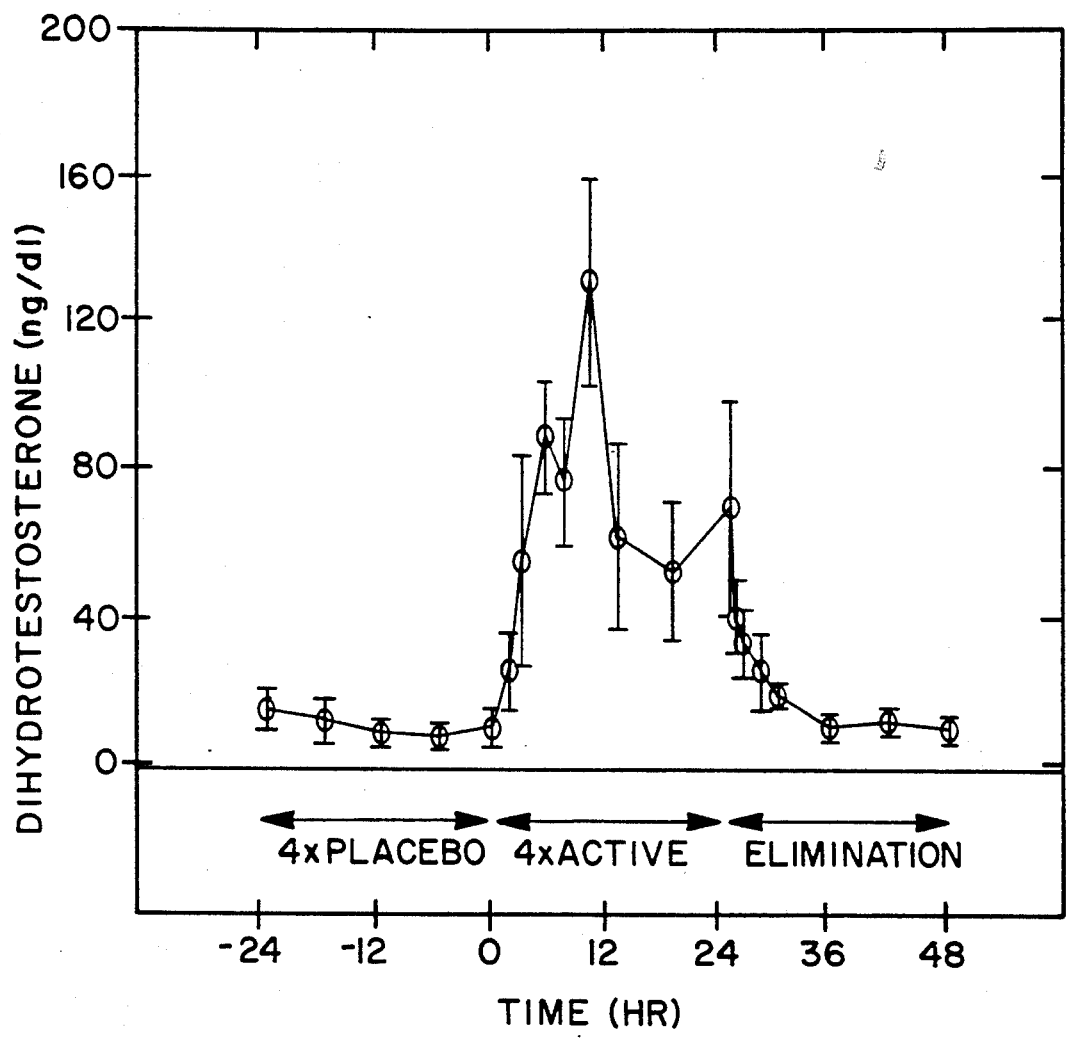

FIGS. 1 and 2 show, respectively, the testosterone and DHT levels resulting from these tests.

Figure 3:
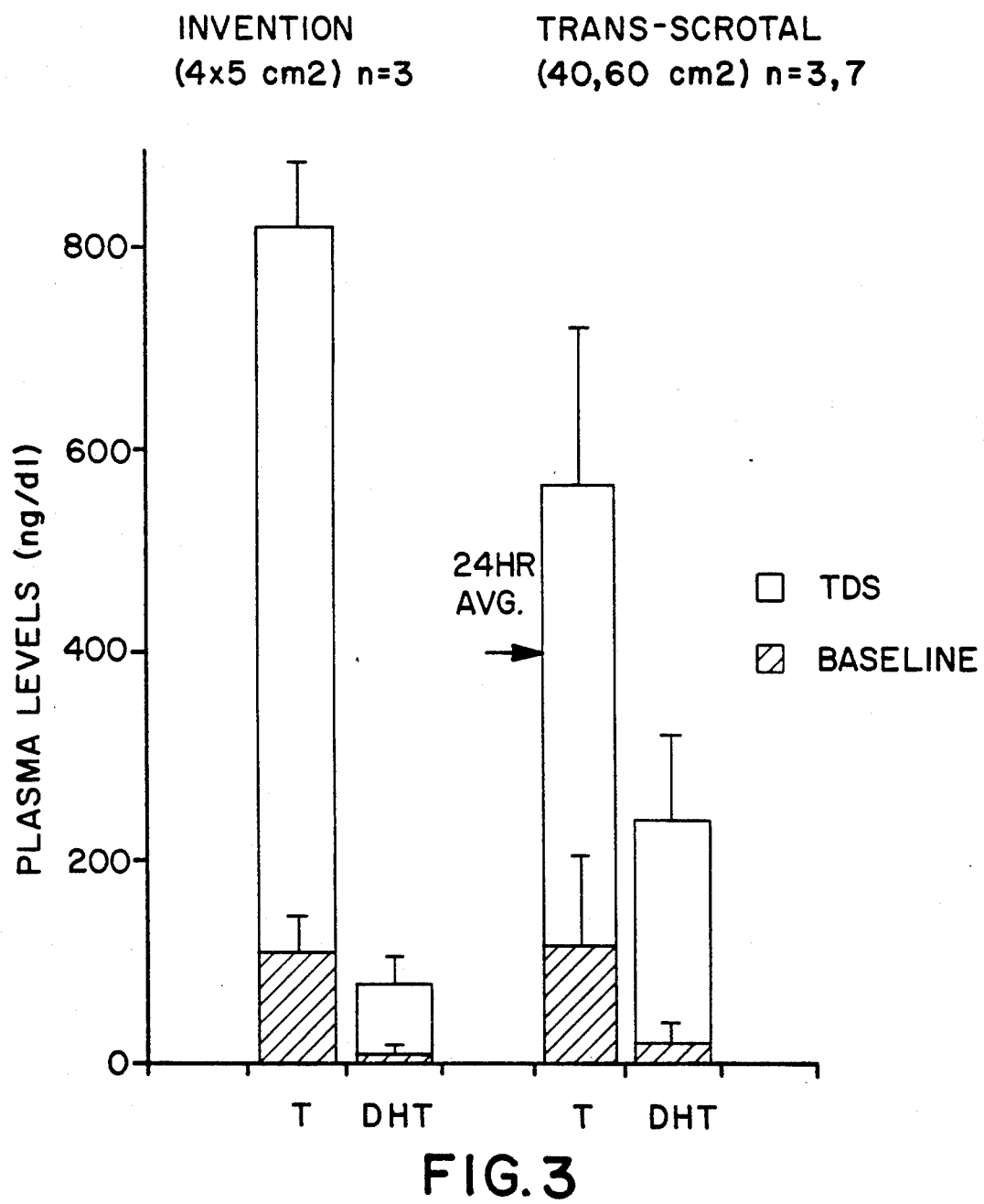
FIGS. 3 and 4 are bar graphs comparing the results of the tests described in Example 2 with the prior art.

FIG. 3 shows a comparison of the testosterone and DHT blood levels provided by the composite of this example and by the ALZA transscrotal system as reported by Findlay, suora. As shown, the blood levels of testosterone provided by the composite of this example are significantly higher than those provided by the transscrotal system. Correspondingly, the blood levels of DHT are significantly lower for the composite of this example as compared to the transscrotal system.

Figure 4:
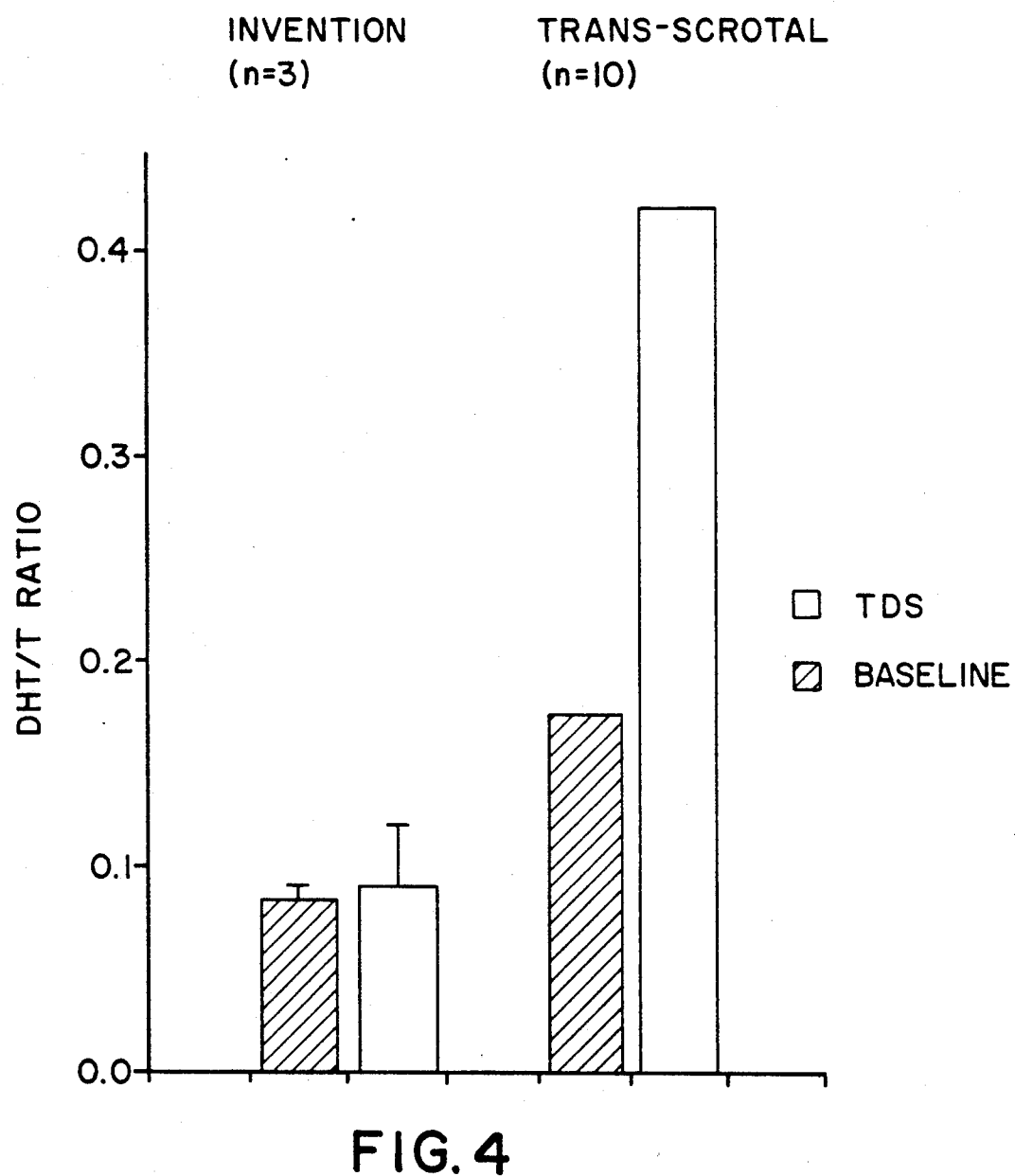

FIG. 4 shows a comparison of the DHT to testosterone ratios provided by the composite of this example and the transscrotal system (again, as reported by Findlay). As shown, the ratio for the composite of this example is significantly less than the ratio for the transscrotal system.

EXAMPLE 3

A laminated composite of the same structure as that of Example 2 was prepared except that the ointment composition was: 12.4 mg testosterone, 342.40 mg ethanol, 123.40 mg water, 311.90 mg glycerin, 19.2 mg GMO, 19.9 mg ML, 27.7 mg Carbomer 1342 and 10.2 mg 2 N NaOH. The reservoir cavity surface was 7.5 $cm^2$.

Figure 5:
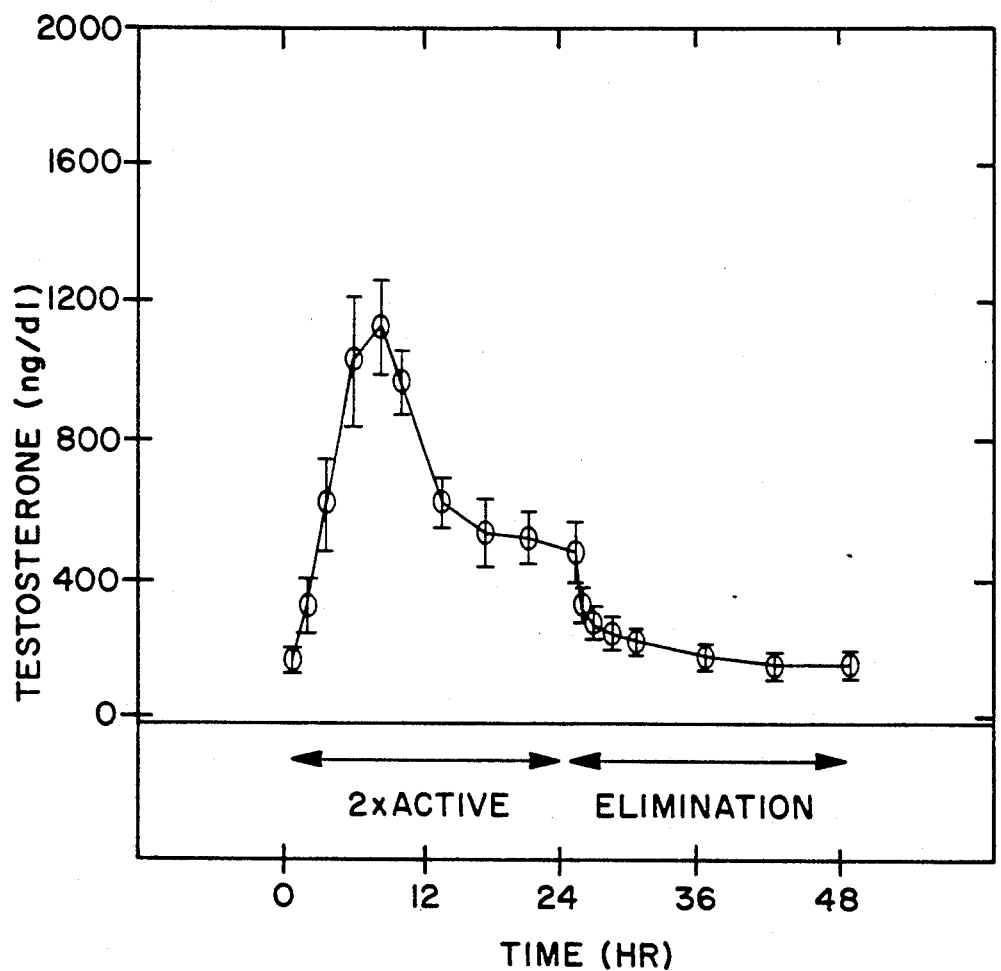
FIGS. 5 and 6 are graphs of the test results of Example 3.
Figure 6:
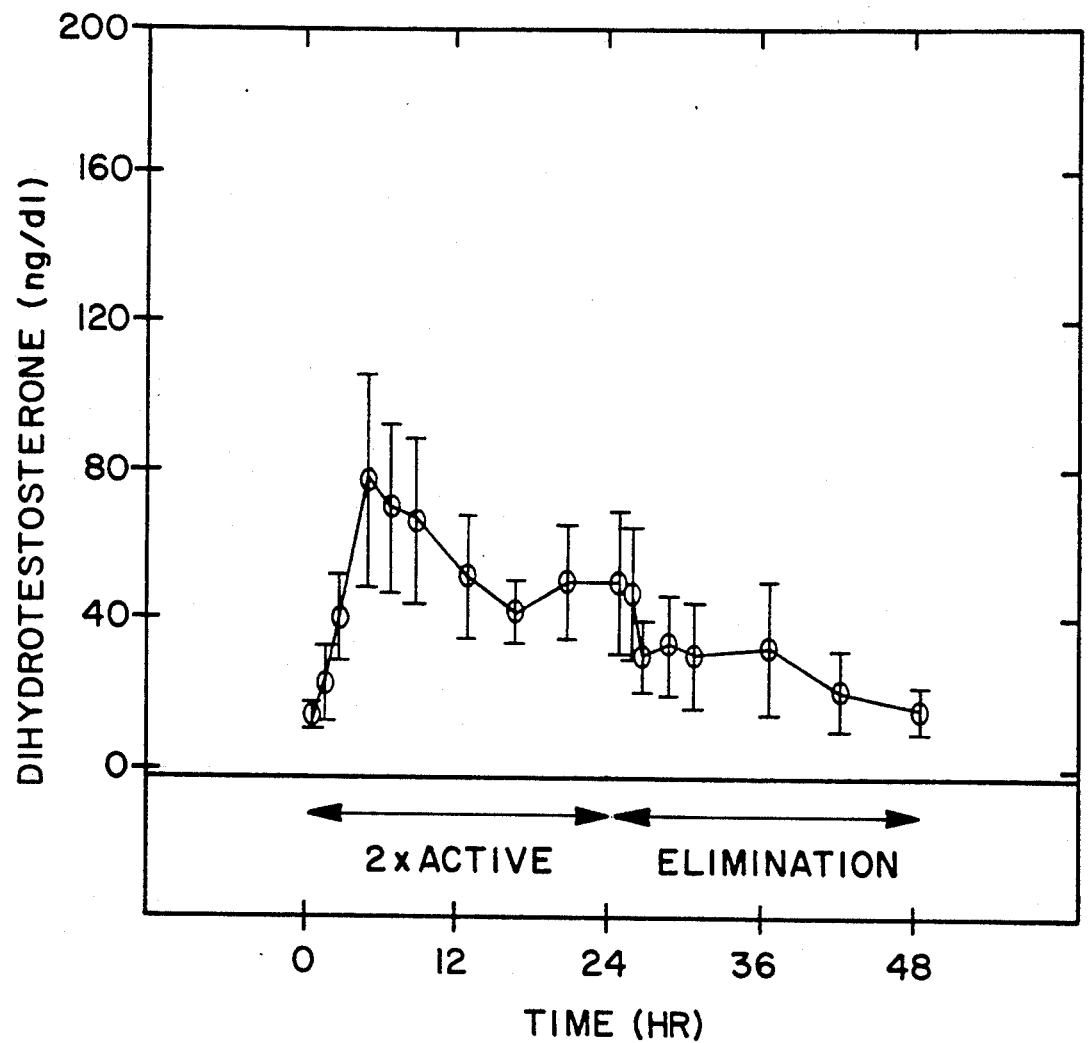

These composites (2 each) were placed on the lower backs of six hypogonadal men for 24 hr. Blood was sampled periodically over that period and their testosterone and DHT levels determined as in Example 2. FIGS. 5 and 6 report the results of these tests.

Figure 8:
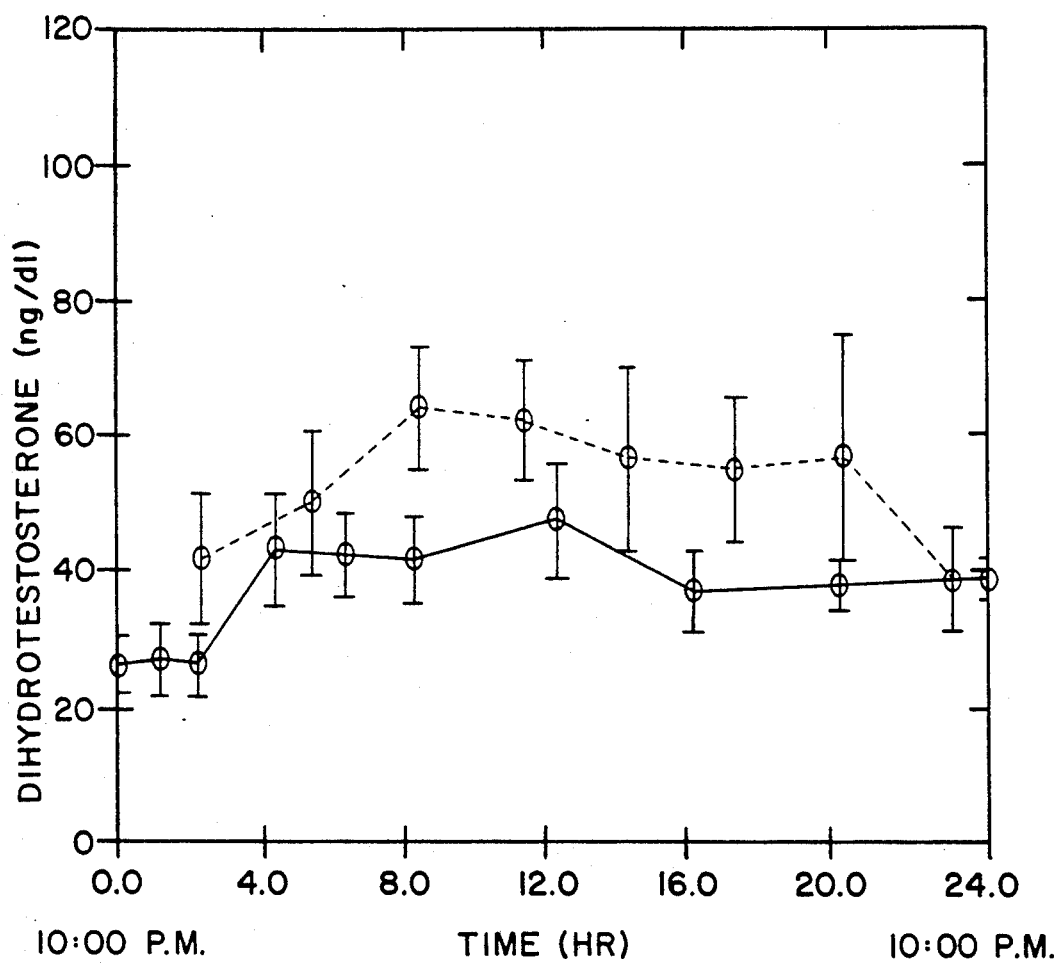
Figure 9:
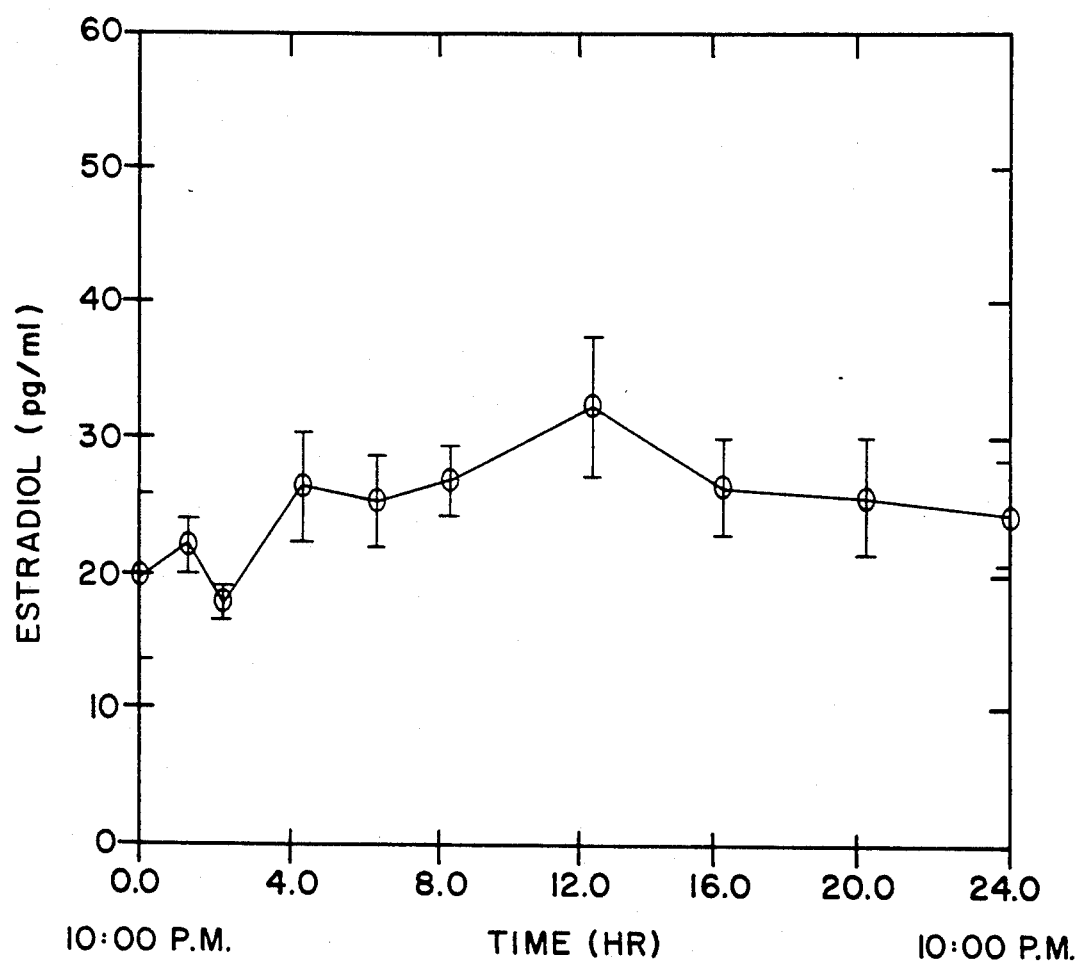

FIGS. 7, 8 and 9 depict average 24 hr plasma levels for testosterone, DHT, and E2 in five hypogonadal subjects following 28 days of continuous transdermal dosing as described above. Open circles in FIGS. 7 and 8 depict average testosterone and DHT levels determined in 12 normal male volunteers. These data demonstrate that physiological levels and circadian rhythms of testosterone and its active metabolites can be achieved and maintained using nonscrotal transdermal delivery systems according to the present invention.

Modifications of the above described modes for carrying out the invention that are obvious to those of skill in the fields of transdermal drug delivery pharmacology and medicine are intended to be within the scope of the following claims.

We claim:

1. A device for administering testosterone transdermally across an area of unbroken nonscrotal skin at a flux from 5 to 30 $\mu g/cm^2/hr$ comprising:
   (a) a reservoir comprising testosterone dissolved in a carrier, and a skin permeation enhancer, the amount and solubility of testosterone in the carrier defining a condition of subsaturation that causes enhanced permeation of testosterone through nonscrotal skin and wherein the combined permeation enhancement resulting from said condition of subsaturation and said permeation enhancer provide said flux; and
   (b) means for maintaining the reservoir in diffusional communication with said area of unbroken nonscrotal skin.

2. The device of claim 1 wherein the flux is from 10 to 20 $\mu g/cm^2/hr$.

3. The device of claim 1 wherein the carrier is a fluid.

4. The device of claim 3 wherein the carrier is ethanol and water.

5. The device of claim 4 wherein the permeation enhancer comprises glycerol monooleate and methyl laurate in combination with the ethanol.

6. The device of claim 5 wherein the ethanol constitutes 20% to 70% by volume of the reservoir, the glycerol monooleate constitutes 0.5% to 5% by volume of the reservoir and the methyl laurate constitutes 0.5% to 5% by volume of the reservoir.

7. The device of claim 1 wherein the amount of testosterone in the reservoir is 5 to 50 mg.

8. The device of claim 6 wherein the amount of testosterone in the reservoir is 10 to 20 mg.

9. The device of claim 1 wherein the concentration of testosterone in the carrier is between 10% and 80% of saturation.

10. The device of claim 8 wherein the concentration of testosterone in the carrier is between 15% and 30% of saturation.

11. The device of claim 5 wherein the reservoir contains 5% to 50% by volume glycerin.

12. The device of claim 10 wherein the reservoir contains 20% to 30% by volume glycerin.

13. The device of claim 1 wherein said area is between 5 and 40 $cm^2$.

14. A method of providing testosterone therapy to a male human comprising placing the device of claim 1 on an area of nonscrotal skin of the human.

15. A method of providing testosterone therapy to a male human comprising placing the device of claim 5 on an area of nonscrotal skin of the human.

* * * * *